United States Patent [19]
Gaynor et al.

[11] Patent Number: 6,001,964
[45] Date of Patent: *Dec. 14, 1999

[54] PEPTIDES WHICH BIND TO ANTI-DOUBLE STRANDED DNA ANTIBODY

[75] Inventors: Bruce D. Gaynor, Pelham; Betty A. Diamond, Bronx; Matthew D. Scharff, Larchmont; Philippe Valadon, New York, all of N.Y.

[73] Assignee: Albert Einstein College of Medicine of Yeshiva University, Bronx, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/531,832

[22] Filed: Sep. 20, 1995

[51] Int. Cl.⁶ ............................... C07K 7/06; C07K 7/08
[52] U.S. Cl. ................... 530/330; 530/324; 530/325; 530/326; 530/327; 530/328; 530/329; 530/387.9; 530/387.1
[58] Field of Search ..................... 435/7.92, 7.1, 435/4; 530/330, 324–329, 387.9, 387.1; 514/17

[56] References Cited

PUBLICATIONS

Katz et al, S. Exp. Med., vol. 180, pp. 925–9832, (Sep. 1994).
Gaynor et al.PNAS, vol. 94, pp. 1955–1960, (Mar. 1997).
Cwirla et al. PNAS, vol. 87, pp. 6378–6382, (Aug. 1990).
Devlin et al, Science, vol. 249, pp. 404–406, (Jul. 1990).
Houghten et al, Nature, vol. 354, pp. 84–86, (Nov. 1991).
Chow et al., The Journal of Biol. Chemistry, vol. 259, (19), pp. 12220–12225, (1984).
Lory et al, J. Exp. Med., vol. 174, pp. 1639–1652, (Dec. 1991).
Yamada et al., J. Biochem., vol. 79, pp. 1223–1234 (1976).
Dokumov et al, British Journal of Obsterics and Gynaecology vol. 88, pp. 126–128 (Feb. 1981).

*Primary Examiner*—Keith D. MacMillan
*Assistant Examiner*—T. D. Wessendorf
*Attorney, Agent, or Firm*—Amster, Rothstein & Ebenstein

[57] ABSTRACT

The present invention provides a method for identifying a peptide which binds to an anti-double stranded DNA antibody. The present invention also provides a class of peptides identified by the method of the present invention which bind to anti-double stranded DNA antibodies and compositions containing these peptides. The present invention also provides methods for the diagnosis and treatment of systemic lupus erythematosus utilizing the peptides of the present invention.

46 Claims, 2 Drawing Sheets

PEPTIDES WHICH BIND TO ANTI-DOUBLE STRANDED DNA ANTIBODY

BACKGROUND OF THE INVENTION

Systemic lupus erythematosus (SLE) is a chronic, inflammatory, often multisystemic disease which can be acute or insidious in onset. SLE is marked by a wide variety of abnormalities, including arthritis and arthralagias, nephritis, central nervous system manifestations, pleurisy, pericarditis, leukopenia or thrombocytopenia, and hemolytic anemia. One of the most serious complications of SLE is lupus nephritis. Renal involvement usually occurs early in the course of the illness and is the leading cause of death in SLE patients.

Diagnosis of SLE is made on the basis of a number of clinical symptoms such as the so-called "butterfly rash," an erythematous rash which frequently appears on the cheeks of afflicted individuals, crossing the bridge of the nose and becoming more pronounced upon exposure to sunlight; and arthritis which can affect any joint system. However, diagnosis is difficult to verify without appropriate laboratory tests. In this regard, antibodies directed to double-stranded DNA (dsDNA) are diagnostic of SLE and serum titers correlate with disease activity in both humans and mice (Pearson et al., J.Immunol. 126:16 (1981)).

Although the role of DNA as the significant target antigen of the so called "anti-dsDNA antibodies" which are diagnostic of SLE, is controversial, it is accepted that the anti-dsDNA antibodies play a significant part in the pathogenesis of the disease, especially its nephritic manifestations, e.g. a secreted form of an anti-dsDNA antibody encoded on a transgene was shown to cause SLE-like glomerulonephritis in a nonautoimmune mouse (Tsao et al., J.Immunol. 149:350 (1992)). Furthermore, the high level and wide variety of autoantibodies against nuclear constituents, especially DNA, and cytoplasmic cellular components detectable in afflicted individuals suggests that the disease represents a failure of the regulatory mechanisms of the autoimmune system that sustain self-tolerance and prevent the body from attacking its own cells, cell constituents, and proteins.

Currently, there is no uniform treatment available for SLE. The choice of treatment regimen usually is determined by the individual patient's symptomatology and health status. There is thus the need for a uniform treatment regimen, especially for the nephritic manifestations of SLE.

The present invention provides a method for identifying peptide sequences which bind to anti-dsDNA antibodies. The present invention also provides peptide sequences which define epitopes recognized by pathogenic murine anti-dsDNA antibodies. The present invention also provides an accurate and rapid method of detecting anti-dsDNA antibodies and of diagnosing SLE which can used by unskilled individuals. The methods of detection and diagnosis of the present invention are based on the detection of the complexes formed between the anti-dsDNA antibodies present in a biological sample and one or more of the peptides of the present invention. The present invention further provides a method of treating SLE using one or a mixture of two or more of the peptides of the present invention to block the harmful results which occur whenever the anti-dsDNA antibodies interact with their target in vivo.

SUMMARY OF THE INVENTION

The present invention provides a method for identifying a peptide which binds to an anti-double stranded DNA antibody which comprises: (a) contacting a peptide library composed of randomly generated peptide sequences with an anti-double stranded DNA antibody; (b) detecting the formation of a complex between the anti-double stranded DNA antibody and a peptide; (c) isolating and purifying the peptide; and (d) sequencing the peptide.

The present invention also provides a peptide which binds to an anti-double stranded DNA antibody, and provides a composition comprising at least one peptide which binds to an anti-double stranded DNA antibody.

In addition, the present invention provides methods for detecting the presence of an anti-dsDNA antibody in a biological sample and for diagnosing systemic lupus erythematosus. The methods comprise the steps of contacting a biological sample collected from a subject with at least one peptide which binds to an anti-double stranded DNA antibody and detecting formation of a complex between the peptide(s) and the anti-double stranded DNA antibody.

The present invention further provides a method for treating systemic lupus erythematosus in a subject in need of such treatment comprising administering to the subject at least one peptide which binds to an anti-double stranded DNA antibody in an amount effective to treat systemic lupus erythematosus.

DETAILED DESCRIPTION OF THE INVENTION

Figure 1A:
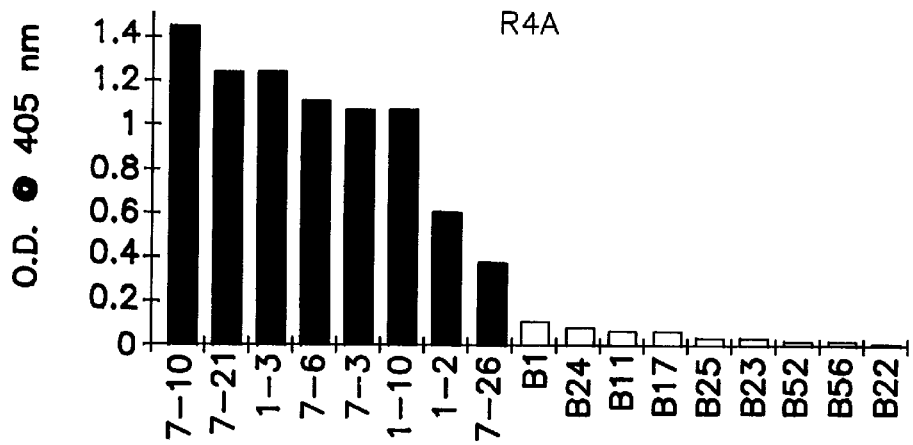
FIG. 1 is comprised of FIGS. 1A, 1B and 1C, and depicts the binding by Enzyme Linked ImmunoSorbent Assay of monoclonal antibodies R4A (FIG. 1A), 95 (FIG. 1B) and 52b3 (FIG. 1C) to phage clones. In each figure, the shaded columns are R4A-selected phage and unshaded columns are 52b3-selected phage.

The present invention provides a method for identifying peptides which bind to anti-double stranded DNA antibodies. According to the method of the present invention, peptides which bind to anti-double stranded DNA antibodies are identified by screening a peptide library with an anti-double stranded DNA antibody and detecting the formation of complexes between the anti-double stranded DNA antibody and the peptides contained in the library. Peptides thus detected are isolated and purified and their amino acid sequence determined.

The anti-double stranded DNA antibodies used to screen the peptide library in the method of the present invention may be animal or human and are preferably human. The anti-double stranded DNA antibodies may be generated by a number of methods known to one skilled in the art. For example, human monoclonal anti-double stranded DNA antibodies may be produced by Epstein Barr virus (EBV) transformed cell lines derived from patients suffering form SLE. Mononuclear cells are isolated by centrifugation of peripheral blood lymphocytes, bone marrow or spleen cells obtained from SLE patients. The mononuclear cells are mixed with an EBV-infected Marmoset cell line. The transformed cells which result from this procedure are cloned.

The monoclonal antibodies produced by the EBV-transformed cell lines may be tested for DNA reactivity by a number of methods known to one skilled in the art, e.g. labeled DNA made double stranded by filtration through nitrocellulose filters, is incubated with antibody and the amount of label retained by the filter measured to assess DNA binding by the antibody (Mannheimer-Lory, et al., *J.Clin.Invest.* 87:1519–1525 (1991)).

The peptide libraries used in the method of the present invention contain peptides composed of variable, randomly-generated peptide sequences. The peptides may be of uniform or non-uniform length. Such libraries may be prepared by a number of procedures known in the art. These procedures may involve the use of peptides produced by the application of recombinant DNA technology as outlined in the Experimental Details Section which follows. For example, oligonucleotides of random sequence are inserted into a phage gene so that the peptide encoded by the oligonucleotide is expressed during the lifecycle of the phage. Alternatively, the peptides may be synthesized by automated means such as the peptide synthesis systems manufactured and supplied by Applied Biosystems (Foster City, Calif.). Such peptide synthesis systems are well known to one skilled in the art, e.g. Synergy Personal Peptide Synthesizer (Model 432).

The peptide library may be screened using the anti-double stranded DNA antibody by methods well known in the art, e.g., immunoprecipitation. Such methods are discussed in greater detail below. Several isotopic (e.g. $^{125}$I) and nonisotopic (e.g. chemiluminiscent) means may be used to detect complex formation between the peptide and the anti-double stranded DNA antibody. Other means of detection would be apparent to one skilled in the art.

Once a particular phage has been identified as encoding a peptide which binds to an anti-double stranded DNA antibody, the peptide is isolated by separating the peptide from the antibody (e.g., by using denaturing conditions), and purified by standard techniques well known to one skilled in the art such as conventional chromatographic techniques. Following isolation and purification of the peptide, its amino acid sequence can then be determined. Means for determining the amino acid sequences of peptides are well known in the art, e.g., the Microsequence Analysis System—Model 476A (Applied Biosystems).

The present invention also provides a class of peptides which bind to anti-double stranded DNA antibodies and are detected by the above-outlined method. These peptides are between about 5 and about 50 amino acids in length, and may be between about 5 and about 30, about 5 and about 15, about 5 and about 13 and about 5 and about 10 amino acids in length. Shorter peptides are preferred for diagnostic and therapeutic applications. The peptides of the present invention are monomers with amino acids joined through amide bonds. In the context of this specification, the amino acids may be the L- or D-optical isomer. Standard abbreviations for amino acids are used herein (e.g. Pro for Proline). These abbreviations are included in Stryer, *Biochemistry,* Third Ed. (1988) which is incorporated herein in its entirety by reference.

One peptide of the present invention binds to human anti-dsDNA monoclonal antibodies and contains the general contiguous amino acid sequence X-Gly-Trp-X-Arg-Val (SEQ ID NO:2), wherein X represents any amino acid known in the art. Thus examples of the peptides of the present invention include but are not limited to peptides with the following amino acid sequence:

Trp-Gly-Trp-Thr-Arg-Val (SEQ ID NO:2);
Leu-Gly-Trp-Val-Arg-Val (SEQ ID NO:2); and
Phe-Gly-Trp-Thr-Arg-Val (SEQ ID NO:2).

Another peptide of the present invention binds to human anti-double stranded DNA monoclonal antibodies and contains the general amino acid sequence X-Trp-X-Tyr-His-X (SEQ ID NO:3), wherein X represents any amino acid sequence known in the art. Thus examples of the peptides of the present invention include but are not limited to peptides with the following amino acid sequence:

Trp-Trp-Val-Tyr-His-Pro (SEQ ID NO:3); and
Tyr-Trp-Tyr-Tyr-His-Trp (SEQ ID NO:3).

Another peptide of the present invention binds to mouse anti-double stranded DNA monoclonal antibodies and contains the general amino acid sequence X1-Trp-X1-Tyr-X2 (SEQ ID NO:4), wherein X1 is Asp or Glu, and X2 is Gly or Ser. Thus the present invention includes peptides with the following amino acid sequence:

Asp-Trp-Asp-Tyr-Gly (SEQ ID NO:4);
Asp-Trp-Glu-Tyr-Gly (SEQ ID NO:4);
Glu-Trp-Asp-Tyr-Gly (SEQ ID NO:4);
Glu-Trp-Glu-Tyr-Gly (SEQ ID NO:4);
Asp-Trp-Asp-Tyr-Ser (SEQ ID NO:4);
Asp-Trp-Glu-Tyr-Ser (SEQ ID NO:4);
Glu-Trp-Asp-Tyr-Ser (SEQ ID NO4);
Glu-Trp-Glu-Tyr-Ser (SEQ ID NO:4).

Another peptide of the present invention binds to mouse anti-dsDNA monoclonal antibodies and contains the general amino acid sequence X1-Gly-X1-Trp-Pro-Arg (SEQ ID NO:5), wherein X1 is Asp or Glu. Thus the present invention includes peptides with the following amino acid sequences:

Asp-Gly-Asp-Trp-Pro-Arg (SEQ ID NO:5);
Glu-Gly-Asp-Trp-Pro-Arg (SEQ ID NO:5);
Asp-Gly-Glu-Trp-Pro-Arg (SEQ ID NO:5);
Glu-Gly-Glu-Trp-Pro-Arg (SEQ ID NO:5).

The peptides of the present invention may be synthesized and purified by a number of established procedures known in the art such as the so-called "Merrifield" solid phase peptide synthesis described in Merrifield, *J.Am.Chem.Soc.* 85:2149–2154 (1963). Solid phase synthesis techniques have been provided for the synthesis of several peptide sequences on substrates such as "pins" (See, Geysen et al., *J.Immun.Meth.* 102:259–274 (1987)). Other solid-phase techniques involve synthesis of various peptide sequences on different cellulose disks supported on a column (See Frank and Doring, *Tetrahedron* 44:6031–6040). Peptides may also be synthesized using automated peptide synthesizers, e.g. Peptide Synthesizer—Model 431-A (Applied Biosystems).

The peptides of the present invention may be conjugated to a variety of molecules such as detectable markers and toxins or may be synthesized as polymers. Methods for conjugating peptides to such molecules are well known in the art. Suitable detectable markers include but are not limited to radioactive markers such as $^{125}$I, fluorescent markers such as fluorescein, and enzymic markers such as horseradish peroxidase. Suitable toxins include but are not limited to Cholera toxin, Diphtheria toxin, Pertussis toxin, *E.coli* heat-labile toxin, *E.coli* heat-stable toxin, Botulinum toxin, Tetanus toxin, and the adenylate cyclases of *Bordetella pertussis* and *Bacillus anthracis,* and any other molecules which are capable of destroying or inactivating any cells or molecules which contain a receptor which binds to the peptides of the present invention. Such cells and molecules include but are not limited to B cells and antibodies.

The present invention also provides a composition comprising one or a mixture of two or more peptides which bind to anti-double stranded DNA antibodies. In a preferred embodiment, the composition of the present invention comprises one or a mixture of two or more peptides together with a pharmaceutically or physiologically acceptable carrier. Such compositions may be prepared by adding one or a mixture of two or more peptides to the pharmaceutically or physiologically acceptable carrier. Suitable pharmaceutically or physiologically acceptable carriers include but are not limited to water containing physiologically compatible substances such as sodium chloride, glycine, and the like, having a buffered pH compatible with physiological conditions to produce an aqueous solution, and rendering said solution sterile. In another embodiment, one or a mixture of two or more peptides can be mixed or otherwise made compatible with buffers and reagents known to those skilled in the art in order to facilitate their use in in vitro applications such as diagnostic assays for SLE antibodies.

The present invention also provides a method for detecting the presence of anti-double stranded DNA antibodies in a biological sample. The method of the present invention comprises contacting the biological sample with one or a mixture of two or more peptides and detecting complex formation between the peptide(s) and anti-double stranded DNA antibodies, if present in the sample. A biological sample may be a bodily fluid e.g., blood or saliva, or a secretion, e.g., sweat or tears. The biological sample may be collected by any means known to those skilled in the art for collecting such samples, e.g., venipuncture in order to obtain a blood sample.

Immunochemical assays for detecting anti-dsDNA antibodies using one or a mixture of two or more peptides can be conducted using a variety of techniques known in the art. For example, a liquid phase assay can be used wherein the peptide(s) and the biological sample are mixed and allowed to form complexes in solution. The complexes so formed can be detected by a number of methods well known in the art. For example, complex formation can be monitored by sodium dodecyl sulphate (SDS) polyacrylamide gel electrophoresis (PAGE) (Davis et al., Basic Methods in Molecular Biology, 2nd. ed., (eds. Appleton & Lange), Section 17-2 (1994)).

Alternatively, a solid phase assay can be used. In the solid phase assays the peptide(s) identified by the method described above is immobilized on a solid phase to form an antigen-immunoadsorbent. The immunoadsorbent is incubated with the biological sample. After an appropriate period of incubation, the immunoadsorbent is separated from the sample (by, for example, sedimentation or centrifugation) and complex formation detected by standard procedures known in the art, e.g., labeled anti-(human IgG) can be used to detect anti-dsDNA antibodies in a biological sample obtained from a human subject. The amount of label associated with the immunoadsorbent can be compared to positive and negative controls to assess the presence or absence of anti-dsDNA antibodies.

The immunoadsorbent can be prepared by adsorbing or coupling peptide(s) to a solid phase. A variety of different types of solid phase can be used, e.g., beads formed of glass, polystyrene, polypropylene, or dextran. Other suitable solid phases include tubes or plates formed from or coated with these materials. Attachment of peptide(s) to the solid phase can be accomplished by covalent or non-covalent bonding techniques, e.g., covalent bonding via an amide or ester linkage or adsorption. After the peptide(s) is affixed to the solid phase, the solid phase can be post-coated with an animal protein, e.g., 3% fish gelatin, in order to reduce nonspecific adsorption of protein to the immunoadsorbent surface.

The immunoadsorbent is then incubated with the sample to be tested for the presence of anti-dsDNA antibodies. If blood is being screened, then the plasma or serum components can be used. For example, the plasma or serum is diluted with normal animal plasma or serum. The plasma or serum diluent is preferably derived from the same animal species that is the source of the anti-(human IgG) antibody. Anti-(human IgG) antibody can be prepared from a variety of sources known in the art, e.g., sheep or goat. The incubation conditions (e.g., pH, temperature, time of incubation) are not crucial and such parameters can be optimized by routine experimentation by one of ordinary skill in the art.

After incubation and separation of the immunoadsorbent from the biological sample, the immunoadsorbent is incubated with the labeled anti-(human IgG) antibody to detect the presence of anti-dsDNA antibodies bound thereto. Detection can be accomplished by a number of methods known in the art, e.g., the immunoadsorbent is incubated with anti-(human IgG) antibody which is labeled with a radioactive material such as $^{125}I$; or labeled with an optical label such as a fluorescent material; or labeled with an enzyme such as horseradish peroxidase. The anti-human antibody can also be biotinylated and labeled avidin used to detect its binding to immunoadsorbent.

Depending upon the choice of label, the evaluation of the presence of anti-dsDNA antibodies can be determined in a variety of ways. Label can be detected by a gamma counter if the label is a radioactive gamma emitter, or by a fluorimeter, if the label is a fluorescent material. In the case of an enzyme, label detection may be accomplished calorimetrically using an enzyme substrate.

For convenience and standardization, reagents for the performance of the various types of immunometric assays made possible by the use of the peptides which bind anti-dsDNA antibodies can be assembled into assay kits. For example, a kit for screening blood for the presence of anti-dsDNA antibodies would include: an immunoadsorbent, e.g., a polystyrene bead coated with a peptide(s); a diluent for the serum or plasma sample, e.g., normal goat serum or plasma; an anti-(human IgG) antibody, e.g., goat anti-(human IgG) antibody in buffered, aqueous solution containing about 1% goat serum or plasma; a positive control; and a negative control. If the label is an enzyme, an additional element of the kit could be the substrate for the enzyme.

The present invention also provides a method of diagnosing SLE which comprises obtaining a biological sample, contacting the biological sample with one or a mixture of two or more peptides using standard procedures already described and well known to those skilled in the art. Complex formation between one or a mixture of two or more of the peptides and antibodies contained in the biological sample is diagnostic of SLE. In particular, such complex formation is indicative of the nephrotoxicity associated with SLE.

The method of the present invention can be used to diagnose SLE in a human or animal, and is preferably used to diagnose SLE in a human. The method of the present invention can specifically be used to determine which patients will develop kidney disease. The biological sample may be obtained and complex formation monitored using the procedures described above.

The present invention also provides a method for treating SLE. In a preferred embodiment of the present invention, the peptides are capable of neutralizing antibodies which are important in the pathogenesis of SLE. Neutralization of the antibody activity occurs as a result of the formation of a stable complex between peptide and antibody molecule or as a result of conformational changes in the antibody molecule which are caused by the binding of peptide and antibody.

Compositions comprising one or a mixture of two or more peptides which bind anti-dsDNA antibodies in combination with pharmaceutically or physiologically acceptable carriers may be prepared as described above and administered using procedures known to one skilled in the art such as intravenous, intramuscular, subcutaneous, or intraperitoneal routes of administration. Other modes of administration would be apparent to one skilled in the art.

The peptide(s) contained in the composition can be protected against degradation by proteases in vivo by a number of methods known to one skilled in the art, e.g., by increasing the concentration of peptides in the peptide composition; more frequent administration of the peptide composition; and chemical protection of peptide(s) using protective groups well known to those skilled in the art of peptide chemistry. Such protective groups will preferably protect the peptide from the effects of proteases and will not interfere with the antibody-peptide binding reaction.

The effective amount of peptide composition and the decision to use a single peptide or a mixture of two or more peptides will depend upon the individual subject being treated. Peptide(s) can be delivered to their site of action in slow-release vehicles known in the art such as liposomal preparations. Such slow-release vehicles can be injected or implanted using surgical procedures. The precise manner of delivery will be dependent upon the subject being treated and such will be obvious to one skilled in the art when presented with the individual subject. The peptides may also be used in polymeric form to induce B cell tolerance.

The present invention is described in the following Experimental Details Section, which sets forth specific examples to aid in an understanding of the invention, and should not be construed to limit in any way the invention as defined in the claims which follow thereafter.

Experimental Details Section

I. Materials and Methods

A. Isolation of Antibodies

Standard hybridoma technology was used to fuse spleen cells from a BALB/c mouse immunized intraperitoneally with phosphorylcholine (PC) (Sigma, Chemical Co., St. Louis, Mo.) conjugated to human gamma globulin in Complete Freund's Adjuvant PC coupled to keyhole limpet hemocyanin (KLH) (100 μg). The monoclonal antibody R4A is encoded by the germline S107 V11 H chain gene and a germline $V_k1$ L chain gene (Shefner et al., J.Ex.Med. 173:287–296 (1991)). SCID mice given R4A cells in vivo display proteinuria and dense immunoglobulin deposition in glomeruli (Scott, et al., Proc. Natl. Acad. Sci. 89:5398–5402 (1994)).

The 52b3 monoclonal antibody was obtained by performing site-directed mutagenesis on the R4A progenitor resulting in three amino acid differences in FR3 of the H chain: Arg was changed to Gln at position 55, Thr was changed to Ala at position 82b and Arg was changed to Ser at position 83. 52b3 shows a 10-fold greater dsDNA binding than R4A. Although SCID mice given 52b3 cells develop proteinuria and display mild antibody deposition in glomeruli, they also have marked deposition in renal tubules.

The 95 monoclonal antibody was obtained by performing site-directed mutagenesis on the R4A progenitor generating a single amino acid change in CDR3 of the H chain: Asp was changed to Gly at position 95. 95 shows no detectable dsDNA binding and SCID mice given 95 cells show no antibody sequestration in glomeruli and no disease.

B. Construction of a Peptide Library

The decapeptide library L100 expressed on the minor coat protein PIII was constructed using the vector fUSE5 (Scott and Smith, Science 249:386–390 (1990)) with the aminoterminus $NH_2$-Ala-Asp-Gly-Ser-Gly-Gly-$X_{10}$-Gly-Ala-Pro-Ser-Gly-Ala-Glu-Thr-Val (SEQ ID NO:6) using standard methods.

C. Isolation of Antibody-Bound Phage Clones

Library screening was performed using modifications of the technique described by Scott and Smith, supra. Three or four rounds of affinity selection were performed. Antibody was incubated for 4 hours with gentle agitation with an aliquot of phage library in 100 μl of biopanning buffer (10 mM Tris/HCl pH 7.5, 150 mM NaCl, 0.1% w/v BSA, 0.1% v/v TWEEN 20 (polyoxyethylenesorbitan monolaurate), 0.02% w/v $NaN_3$). Antibody concentration was 1 μM for the first round and 10 nM for the subsequent rounds of biopanning.

For the first round of biopanning, 50 μl of streptavidin coated magnetic beads (Advanced Magnetics, Inc., Cambridge, Mass.) were incubated with 100 μl of 5 μM biotinylated protein G (Pierce, Rockford, Ill.) for 1 hour at room temperature with agitation. In subsequent rounds of biopanning 10 μl of streptavidin beads and 0.05 μM of biotinylated protein G were used. To saturate the streptavidin sites on the beads, 1 μl of free D-biotin 10 mM (Sigma Chemical Co., St. Louis, Mo.) was added and incubated for 15 minutes at room temperature with continued agitation. Beads were washed three times with 500 μl of biopanning buffer (BPB) using an Eppendorf magnetic particle concentrator (DYNAL, Oslo, Norway).

The streptavidin bead/biotinylated protein G complex was combined with the phage library/antibody mixture and incubated for 30 minutes at room temperature with agitation. Beads were collected and unbound phage were removed by washing. Phage were eluted with 100 μl of 0.1M glycine pH 2.2 for 10 minutes and neutralized with 10 μl 2M Tris pH 9.0.

Eluted phage were amplified on E.coli K91Kan (Scott, et al., supra) and used as input in the subsequent rounds of biopanning. After three or four rounds individual phage clones were randomly selected for sequencing using Sequenase Version 2.0 (United States Biochemical, Cleveland, Ohio) and fUSE $^{35}S$ sequencing primer. Sequencing was performed according to the dideoxy chain termination method of Sanger, et al. (Sanger et al., PNAS 74:5463–5467 (1977)).

D. Enzyme-Linked ImmunoSorbent Assay

Binding of antibodies to phage was determined by Enzyme-Linked ImmunoSorbent Assay (ELISA). Microtiter plates (Becton Dickinson, Lincoln Park, N.J.) were coated with 50 μl of antibody (1 μg/ml unless otherwise specified) in TBS (Tris/10 mM HCl pH 7.5, 150 mM NaCl) overnight at 4° C. Plates were washed 3 times with TBS/0.05% TWEEN 20 (polyoxyethylenesorbitan monolaurate). Approximately $2.5 \times 10^{10}$ purified phage in 50 μl TBS were added to each well, incubated for 2 hours at 37° C., washed, and then were blocked with 150 μl of TBS/2% BSA for 1 hour at 37° C. Plates were incubated with 50 μl of a 1:4000 dilution in TBS of biotinylated sheep antibody to M13 phage (5'→3', Inc., Boulder, Colo.) for 1 hour at 37° C. Plates were washed again and incubated with a 1:4000 dilution of alkaline phosphate-conjugated streptavidin (Southern Biotech. Assoc. Inc., Birmingham, Ala.) and developed with Sigma-104 substrate tablets (Sigma Chemical Co.). Optical density was read at 405 nm.

E. Peptide Synthesis

The amidated, acetylated peptides Asp-Trp-Glu-Tyr-Ser-Val-Trp-Leu-Ser-Asn (SEQ ID NO:1), Asp-Trp-Glu-Tyr-Ser (SEQ ID NO:4), and Arg-His-Glu-Asp-Gly-Asp-Trp-Pro-Arg-Val (SEQ ID NO:7) were synthesized in the Macromolecular Analysis Facility at the Albert Einstein College of Medicine.

II. Results

The monoclonal antibodies R4A and 52b3 were individually reacted with the phage library in order to obtain peptide sequences recognized by each antibody. Three rounds of biopanning were performed with R4A and four with 52b3 resulting in substantial enrichment (Table 1). Selected phage were randomly chosen for sequencing. A distinct consensus motif could be identified in each case (Tables 2 and 3). The dominant motif for R4A was Asp/Glu-Trp-Asp/Glu-Tyr-Ser/Gly (SEQ ID NO:4). Selected peptides had an internal cysteine bridge which presumably constrains the conformation of the internal sequence; some of these sequences also expressed the dominant motif.

The motif identified for 52b3 is Asp/Glu-Gly-Asp/Glu-Trp-Pro-Arg (SEQ ID NO:5). Peptides with internal cysteine bridges were also isolated with 52b3, although the internal sequence of these were unlike the linear motif.

Figure 1B:
Figure 1C:
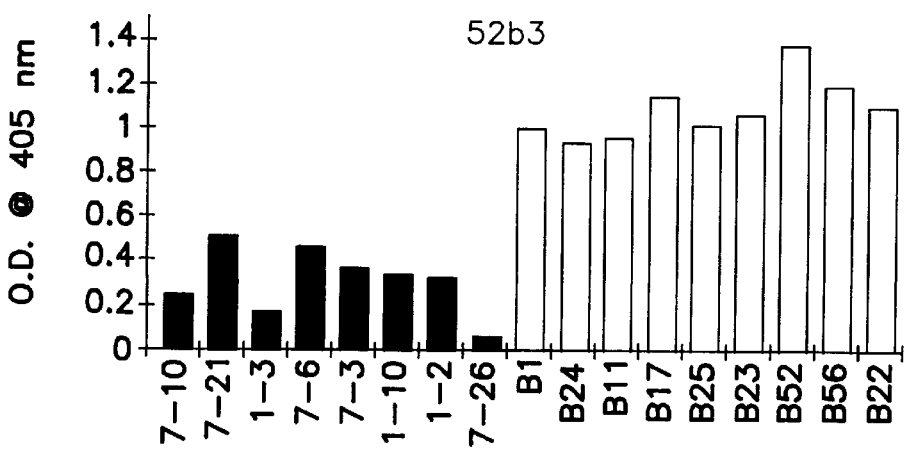

In order to confirm binding of R4A or 52b3 to these phage, ELISAs were performed. All selected phage were bound by the selecting antibody (FIG. 1). R4A bound only those phage isolated by selection with R4A; 52b3 bound much more strongly to 52b3 selected phage than the R4A selected phage. Antibody 95, which differs from R4A by a single amino acid in the heavy chain and from 52b3 by four amino acids in the heavy chain, and has no detectable finding to dsDNA, did not bind to any of the phage clones recognized by either R4A or 52b3.

Figure 2:
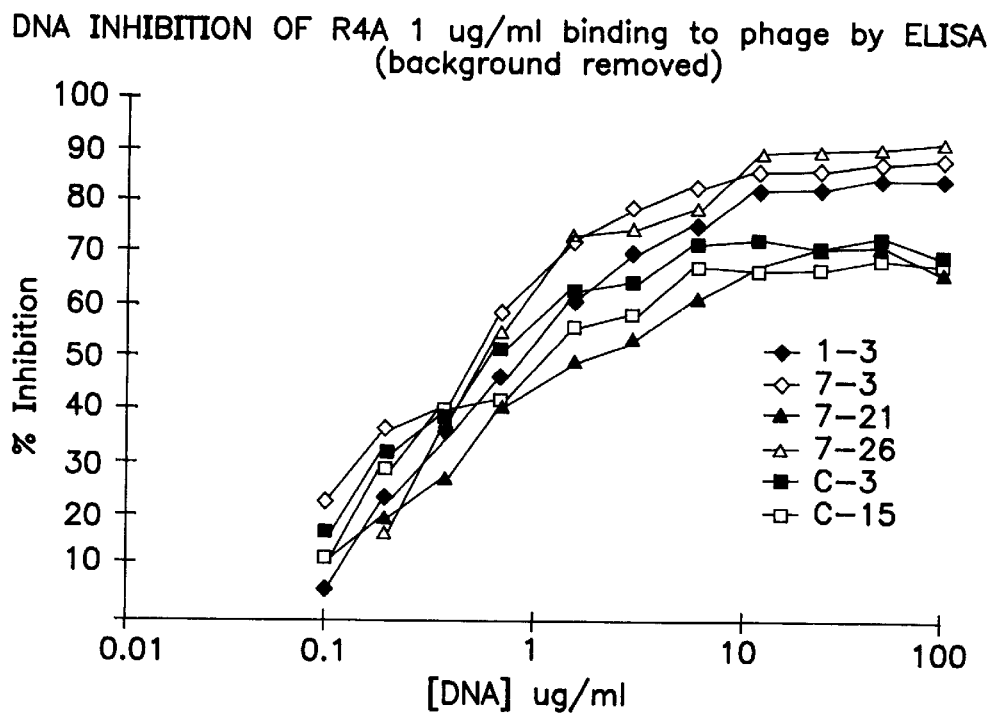
FIG. 2 depicts the inhibition of R4A (1 µg/ml) binding to peptide Asp-Trp-Glu-Tyr-Ser-Val-Trp-Leu-Ser-Asn (SEQ ID NO:1) by calf thymus DNA. Binding is measured by Enzyme Linked ImmunoSorbent Assay.
Figure 3:
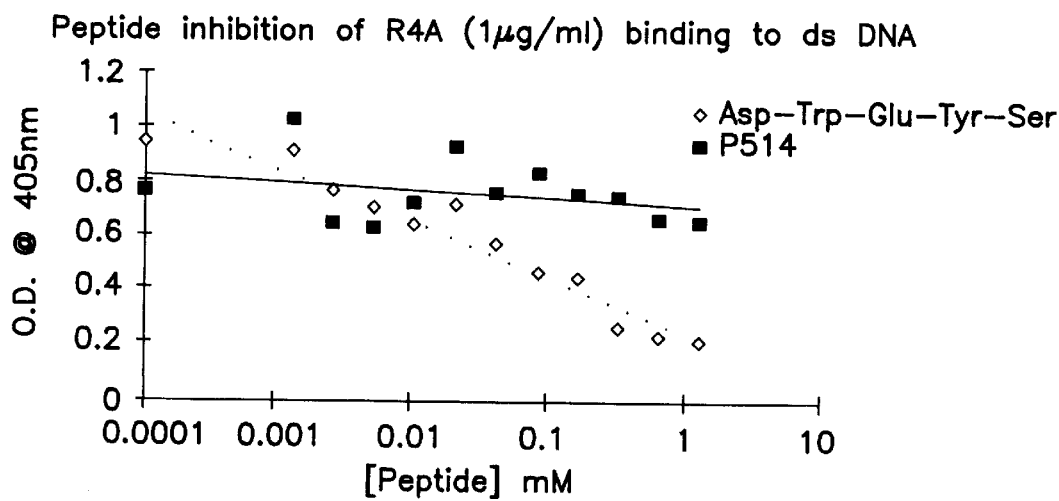
FIG. 3 depicts peptide inhibition of R4A (1 µg/ml) binding to calf thymus double stranded DNA by Enzyme Linked ImmnunoSorbent Assay.

To determine whether peptide and dsDNA bound within the same antigen binding site of each antibody, inhibition assays were performed with specific peptides. Calf thymus DNA inhibited the binding of R4A and 52b3 to R4A and 52b3 selected phage, respectively (FIG. 2). In addition, selected phage inhibited the binding of antibody to dsDNA. These were used in fluid phase to inhibit the binding of antibody to dsDNA. Two peptides, Asp-Trp-Glu-Tyr-Ser-Val-Trp-Leu-Ser-Asn (SEQ ID NO:1) and Asp-Trp-Glu-Tyr-Ser (SEQ ID NO:4), were chosen as the R4A specific epitope; the 52b3 specific peptide was Arg-His-Glu-Asp-Gly-Asp-Trp-Pro-Arg-Val (SEQ ID NO:7). Each peptide inhibited dsDNA binding by the appropriate antibody only (FIG. 3). This result confirmed that the peptides were dsDNA mimotopes binding in or very close to the same site as dsDNA and also emphasized the utility of peptides as probes for differences in the antigen binding pocket of highly related antibody molecules.

III. Discussion

While it has been documented for several years that antibodies may bind more than one antigen in a single antigen binding pocket, peptide libraries provide an unprecedented opportunity to probe the cross-reactivity of particular antibody molecules. An analysis of the peptides contained in phage isolated by a given monoclonal antibody demonstrates that multiple antigenic epitopes may fit within a single binding site. Furthermore, by using peptide libraries to probe antibody binding sites it has been possible to show that an anticarbohydrate antibody can also bind a peptide mimotope (Devlin, et al., Science 249:404–406 (1990)) and that cross-reactive antigens need not have obviously homologous structures (Balass, M., PNAS 90:10638–10642 (1993); Devlin et al., Science 249:404–406 (1990)). We have shown that antibodies that bind dsDNA may also bind peptide antigens. Both R4A and 52b3 were isolated as dsDNA binding antibodies and both have been shown to bind peptide also. This binding appears by competitive inhibition studies to be within the same site in which dsDNA binds. Furthermore, the peptides bound by R4A are distinct from those bound by 52b3 even though the antibodies are highly homologous, differing by only 3 amino acids in the heavy chain variable region. A second surprising result is that 95 which differs by only a single amino acid from R4A and four amino acids from 52b3 but has no reactivity with dsDNA binds neither R4A nor 52b3 selected peptides. Both R4A and 52b3 bind anionic peptides which is consistent with DNA also having a negative charge. However, 95 which is more cationic reflecting a Asp to Gly substitution in CDR3 of the heavy chain, does not bind these anionic peptides. Thus the negative charge is not sufficient for these peptides or for dsDNA binding to 95.

The motifs for both pathogenic antibodies have the Asp/Glu-X-Asp/Glu sequence, suggesting that although acidic residues are important in binding, they do not define the fine specificity difference that causes R4A to deposit in glomeruli and 52b3 to deposit in tubules. It is also noteworthy that both the R4A and 52b3 peptides have aromatic residues, tryptophan and tyrosine.

It is appealing to speculate that the negatively charged aspartate and glutamate residues are analogous to phosphate groups, aromatic tryptophan residues are analogous to the pentose sugar backbone, and the tryrosine and serine residues are analogous to the hydroxyl groups attached to the pentose moiety in the DNA molecule, thus explaining why these peptides are mimotopes of DNA.

One potential utility of identifying peptide mimotopes for dsDNA is to try to determine if the actual eliciting antigen for production of these antibodies or target antigen for deposition in kidneys might be a protein molecule. A search for amino acid sequences with homology to the consensus sequence identified for the R4A and 52b3 monoclonal antibodies revealed that the entire R4A sequence, Asp-Trp-Asp-Tyr-Ser (SEQ ID NO:4), is found in a splice variant of chicken collagen XIV (Walchli, et al., Eur. J. Biochem. 212:483–490 (1993)). It is interesting to speculate whether the murine homolog of chicken collagen XIV also has a splice variant containing the same or highly homologous peptide sequence that would be recognized by the R4A antibody.

All publications mentioned hereinabove are hereby incorporated in their entirety.

While the foregoing invention has been described in some detail for purposed of clarity and understanding, it will be appreciated by one skilled in the art from a reading of the disclosure that various changes in form and detail can be made without departing from the true scope of the invention in the appended claims.

TABLE 1

Yield of phage following biopanning with R4A and 52b3.

| Antibody | Concentration (nM) | Selection Round | Phage Yield (%) with antibody | control | Amplification |
|---|---|---|---|---|---|
| R4A | 1000 | 1 | $6.3 \times 10^{-3}$ | | |
| | 10 | 2 | $1.5 \times 10^{-4}$ | $5.7 \times 10^{-5}$ | 2.6 |
| | 10 | 3 | $1.1 \times 10^{-2}$ | $1.6 \times 10^{-4}$ | 690 |
| 52b3 | 1000 | 1 | $2.0 \times 10^{-2}$ | | |
| | 10 | 2 | $1.6 \times 10^{-2}$ | $1.7 \times 10^{-3}$ | 9.6 |
| | 10 | 3 | $8.9 \times 10^{-2}$ | $1.4 \times 10^{-3}$ | 65 |
| | 10 | 4 | $6.5 \times 10^{-2}$ | $2.7 \times 10^{-4}$ | 239 |

TABLE 2

Randomly selected sequences obtained by biopanning a decapeptide library with R4A. A total of 75 phage were sequenced.

| Phage | Sequence | | | | | | | | | | Frequency | Binding O.D. 405 nm |
|---|---|---|---|---|---|---|---|---|---|---|---|---|
| φ1-3 | | | | D | W | E | Y | S | V | W | L | S | N | 23 | 1.3 |
| φ7-21 | | | W | <u>C</u> | E | A | D | Y | G | R | <u>C</u> | P | | 23 | 1.3 |
| φ7-6 | | | L | Y | F | E | D | Y | R | C | E | L | | 3 | 1.2 |
| φ7-3 | | | | | D | W | D | Y | G | A | L | M | W | A | 1 | 1.1 |
| φ1-10 | | | Y | S | D | W | D | Y | S | E | G | L | | 1 | 1.1 |
| φ1-2 | S | T | E | H | S | E | A | D | L | W | | | | 8 | 0.7 |
| φ7-26 | | V | P | V | <u>C</u> | D | W | E | L | N | <u>C</u> | | | 1 | 0.4 |
| Consensus: | | | | | D/E | W | D/E | Y | S/G | | | | | | |
| φ1-1 | | | | F | S | D | <u>C</u> | Y | H | S | G | <u>C</u> | P | 3 | 1.5 |
| φ3-3 | | | | | | | No insert | | | | | | | | 0.1 |

TABLE 3

Randomly selected sequences obtained by biopanning a decapeptide library with 52b3. A total of 33 phage were sequenced.

52b3 Selected Phage

| Phage | Sequence | | | | | | | | | | Frequency | Binding O.D. 405 nm |
|---|---|---|---|---|---|---|---|---|---|---|---|---|
| φB11 | R | H | E | D | G | D | W | P | R | V | | 1 | 1.4 |
| φB25 | L | L | D | D | G | F | W | P | R | V | | 1 | 1.5 |
| φB23 | C | G | V | D | G | R | W | P | R | W | | 1 | 1.5 |
| φB24 | S | L | I | S | D | E | W | P | R | W | | 1 | 1.3 |
| φB56 | | | | D | G | E | W | P | R | E | G W S | 1 | 1.6 |
| φB22 | E | D | L | E | G | E | W | P | M | R | | 1 | 1.5 |
| φB1 | S | L | D | E | L | D | W | D | S | M | | 4 | 1.4 |
| Consensus: | | | | D/E | G | D/E | W | P | R | | | | |
| φB16 | T | W | <u>C</u> | P | V | W | I | W | D | <u>C</u> | | 1 | 1.0 |
| φB17 | V | L | I | <u>C</u> | W | D | G | <u>C</u> | E | T | | 1 | 1.6 |
| φB21 | W | D | <u>C</u> | Y | V | <u>C</u> | R | L | E | L | | 1 | 1.2 |
| φB52 | S | <u>C</u> | Y | Q | S | Y | P | G | E | <u>C</u> | | 1 | 1.8 |
| φ3-3 | | | | | | No insert | | | | | | | 0.4 |

What is claimed is:

1. A purified peptide which binds to an anti-double-stranded DNA antibody, said peptide being 5 to 30 amino acids in length, and comprising the contiguous amino acid sequence X1-Trp-X1-Tyr-X2, wherein X1 is Asp or Glu, and X2 is Gly or Ser.

2. The peptide of claim 1, being 5 to 15 amino acids in length.

3. The peptide of claim 1, being 5 to 10 amino acids in length.

4. The peptide of claim 1, comprising the contiguous amino acid sequence Asp-Trp-Asp-Tyr-Gly (SEQ.ID.NO.4).

5. The peptide of claim 1, comprising the contiguous amino acid sequence Asp-Trp-Glu-Tyr-Gly (SEQ.ID.NO.4).

6. The peptide of claim 1, comprising the contiguous amino acid sequence Glu-Trp-Asp-Tyr-Gly (SEQ.ID.NO.4).

7. The peptide of claim 1, comprising the contiguous amino acid sequence Glu-Trp-Glu-Tyr-Gly (SEQ.ID.NO.4).

8. The peptide of claim 1, comprising the contiguous amino acid sequence Asp-Trp-Asp-Tyr-Ser (SEQ.ID.NO.4).

9. The peptide of claim 1, comprising the contiguous amino acid sequence Asp-Trp-Glu-Tyr-Ser (SEQ.ID.NO.4).

10. The peptide of claim 1, comprising the contiguous amino acid sequence Glu-Trp-Asp-Tyr-Ser (SEQ.ID.NO.4).

11. The peptide of claim 1, comprising the contiguous amino acid sequence Glu-Trp-Glu-Tyr-Ser (SEQ.ID.NO.4).

12. A peptide conjugate comprising a peptide bound to a toxin, said peptide being 5 to 30 amino acids in length, and comprising the contiguous amino acid sequence X1-Trp-X1-Tyr-X2, wherein X1 is Asp or Glu, and X2 is Gly or Ser.

13. The peptide conjugate of claim 12, wherein the peptide is 5 to 15 amino acids in length.

14. The peptide conjugate of claim 12, wherein the peptide is 5 to 10 amino acids in length.

15. The peptide conjugate of claim 12, wherein the toxin is selected from the group consisting of, Cholera toxin, Diphtheria toxin, Pertussis toxin, *E. coli* heat labile toxin, *E. coli* heat-stable toxin, Botulinum toxin, Tetanus toxin, the adenylate cyclases of *Bordatella pertussis,* and the adenylate cyclases of *Bacillus anthracis.*

16. The peptide conjugate of claim 12, said peptide comprising the contiguous amino acid sequence Asp-Trp-Asp-Tyr-Gly.

17. The peptide conjugate of claim 12, said peptide comprising the contiguous amino acid sequence Asp-Trp-Glu-Tyr-Gly.

18. The peptide conjugate of claim 12, said peptide comprising the contiguous amino acid sequence Glu-Trp-Asp-Tyr-Gly (SEQ.ID.NO.4).

19. The peptide conjugate of claim 12, said peptide comprising the contiguous amino acid sequence Glu-Trp-Glu-Tyr-Gly (SEQ.ID.NO.4).

20. The peptide conjugate of claim 12, said peptide comprising the contiguous amino acid sequence Asp-Trp-Asp-Tyr-Ser (SEQ.ID.NO.4).

21. The peptide conjugate of claim 12, said peptide comprising the contiguous amino acid sequence Asp-Trp-Glu-Tyr-Ser (SEQ.ID.NO.4).

22. The peptide conjugate of claim 12, said peptide comprising the contiguous amino acid sequence Glu-Trp-Asp-Tyr-Ser (SEQ.ID.NO.4).

23. The peptide conjugate of claim 12, said peptide comprising the contiguous amino acid sequence Glu-Trp-Glu-Tyr-Ser (SEQ.ID.NO.4).

24. A peptide conjugate comprising a peptide bound to a detectable marker, said peptide being 5 to 30 amino acids in length, and comprising the contiguous amino acid sequence X1-Trp-X1-Tyr-X2, wherein X1 is Asp or Glu, and X2 is Gly or Ser.

25. The peptide conjugate of claim 24, wherein the peptide is 5 to 15 amino acids in length.

26. The peptide conjugate of claim 24, wherein the peptide is 5 to 10 amino acids in length.

27. The peptide conjugate of claim 24, wherein the detectable marker is a radioactive marker or an enzymatic marker.

28. The peptide conjugate of claim 24, comprising the contiguous amino acid sequence Asp-Trp-Asp-Tyr-Gly (SEQ.ID.NO.4).

29. The peptide conjugate of claim 24, comprising the contiguous amino acid sequence Asp-Trp-Glu-Tyr-Gly (SEQ.ID.NO.4).

30. The peptide conjugate of claim 24, comprising the contiguous amino acid sequence Glu-Trp-Asp-Tyr-Gly (SEQ.ID.NO.4).

31. The peptide conjugate of claim 24, comprising the contiguous amino acid sequence Glu-Trp-Glu-Tyr-Gly (SEQ.ID.NO.4).

32. The peptide conjugate of claim 24, comprising the contiguous amino acid sequence Asp-Trp-Asp-Tyr-Ser (SEQ.ID.NO.4).

33. The peptide conjugate of claim 24, comprising the contiguous amino acid sequence Asp-Trp-Glu-Tyr-Ser (SEQ.ID.NO.4).

34. The peptide conjugate of claim 24, comprising the contiguous amino acid sequence Glu-Trp-Asp-Tyr-Ser (SEQ.ID.NO.4).

35. The peptide conjugate of claim 24, comprising the contiguous amino acid sequence Glu-Trp-Glu-Tyr-Ser (SEQ.ID.NO.4).

36. A composition comprising a peptide and a carrier, which binds to an anti-double-stranded DNA antibody, wherein said peptide is 5 to 30 amino acids in length and comprises the contiguous amino acid sequence X1-Trp-X1-Tyr-X2, wherein X1 is Asp or Glu, and X2 is Gly or Ser.

37. The composition of claim 36, wherein the peptide is 5 to 15 amino acids in length.

38. The composition of claim 36, wherein the peptide is 5 to 10 amino acids in length.

39. The composition of claim 36, wherein said peptide comprises the contiguous amino acid sequence Asp-Trp-Asp-Tyr-Gly (SEQ.ID.NO.4).

40. The composition of claim 36, wherein said peptide comprises the contiguous amino acid sequence Asp-Trp-Glu-Tyr-Gly (SEQ.ID.NO.4).

41. The composition of claim 36, wherein said peptide comprises the contiguous amino acid sequence Glu-Trp-Asp-Tyr-Gly (SEQ.ID.NO.4).

42. The composition of claim 36, wherein said peptide comprises the contiguous amino acid sequence Glu-Trp-Glu-Tyr-Gly (SEQ.ID.NO.4).

43. The composition of claim 36, wherein said peptide comprises the contiguous amino acid sequence Asp-Trp-Asp-Tyr-Ser (SEQ.ID.NO.4).

44. The composition of claim 36, wherein said peptide comprises the contiguous amino acid sequence Asp-Trp-Glu-Tyr-Ser (SEQ.ID.NO.4).

45. The composition of claim 36, wherein said peptide comprises the contiguous amino acid sequence Glu-Trp-Asp-Tyr-Ser (SEQ.ID.NO.4).

46. The composition of claim 36, wherein said peptide comprises the contiguous amino acid sequence Glu-Trp-Glu-Tyr-Ser (SEQ.ID.NO.4).

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 10

```
            (B) TYPE:  AMINO ACID
            (C) STRANDEDNESS:  SINGLE
            (D) TOPOLOGY: LINEAR (ii) MOLECULE TYPE:
            (A) DESCRIPTION:  PEPTIDE (iii) HYPOTHETICAL:  YES (iv) ANTI-SENSE:  NO (xi) SEQUENCE DESCRIPTION:  SEQ ID NO: 1:

Asp Trp Glu Tyr Ser Val Trp Leu Ser Asn
1               5                   10

(2) INFORMATION FOR SEQ ID NO:2:

(i) SEQUENCE CHARACTERISTICS:
            (A) LENGTH: 6
            (B) TYPE:  AMINO ACID
            (C) STRANDEDNESS:  SINGLE
            (D) TOPOLOGY: LINEAR (ii) MOLECULE TYPE:
            (A) DESCRIPTION:  PEPTIDE (iii) HYPOTHETICAL:  YES (iv) ANTI-SENSE:  NO (ix) FEATURE:
            (A) NAME/KEY:
            (B) LOCATION:
            (C) IDENTIFICATION METHOD:
            (D) OTHER INFORMATION:  Xaa at 1 and 4 is any amino
                acid (xi) SEQUENCE DESCRIPTION:  SEQ ID NO: 2:

Xaa Gly Trp Xaa Arg Val
1               5

(2) INFORMATION FOR SEQ ID NO:3:

(i) SEQUENCE CHARACTERISTICS:
            (A) LENGTH:  6
            (B) TYPE:  AMINO ACID
            (D) TOPOLOGY: LINEAR (ii) MOLECULE TYPE:
            (A) DESCRIPTION:  PEPTIDE (iii) HYPOTHETICAL:  YES (ix) FEATURE:
            (A) NAME/KEY:
            (B) LOCATION:
            (C) IDENTIFICATION METHOD:
            (D) OTHER INFORMATION:  Xaa at 1, 3 and 6 is any
                amino acid (xi) SEQUENCE DESCRIPTION: SEQ ID NO: 3:

Xaa Trp Xaa Tyr His Xaa
  1           5

(2) INFORMATION FOR SEQ ID NO:4:

(i) SEQUENCE CHARACTERISTICS:
            (A) LENGTH:  5
            (B) TYPE:  AMINO ACID
            (D) TOPOLOGY: LINEAR (ii) MOLECULE TYPE:
            (A) DESCRIPTION:  PEPTIDE
```

```
      (iii) HYPOTHETICAL: YES (ix) FEATURE:
            (A) NAME/KEY:
            (B) LOCATION:
            (C) IDENTIFICATION METHOD:
            (D) OTHER INFORMATION: Xaa at 1 and 3 is Aspartic
                Acid or Glutamic Acid; Xaa at 5 is Glycine
                or Serine (xi) SEQUENCE DESCRIPTION: SEQ ID NO: 4:

Xaa Trp Xaa Tyr Xaa
  1               5

(2) INFORMATION FOR SEQ ID NO:5:

(i) SEQUENCE CHARACTERISTICS:
            (A) LENGTH: 6
            (B) TYPE: AMINO ACID
            (D) TOPOLOGY: LINEAR (ii) MOLECULE TYPE:
            (A) DESCRIPTION: PEPTIDE (iii) HYPOTHETICAL: YES (ix) FEATURE:
            (A) NAME/KEY:
            (B) LOCATION:
            (C) IDENTIFICATION METHOD:
            (D) OTHER INFORMATION: Xaa at 1 and 3 is Aspartic
                Acid or Glutamic Acid (xi) SEQUENCE DESCRIPTION:  SEQ ID NO: 5:

Xaa Gly Xaa Trp Pro Arg
  1               5

(2) INFORMATION FOR SEQ ID NO:6:

(i) SEQUENCE CHARACTERISTICS:
            (A) LENGTH: 25
            (B) TYPE: AMINO ACID
            (D) TOPOLOGY: LINEAR (ii) MOLECULE TYPE:
            (A) DESCRIPTION: PEPTIDE (iii) HYPOTHETICAL: YES (ix) FEATURE:
            (A) NAME/KEY:
            (B) LOCATION:
            (C) IDENTIFICATION METHOD:
            (D) OTHER INFORMATION: Xaa at 7-16 is any amino acid (xi) SEQUENCE DESCRIPTION: SEQ ID NO: 6:

Ala Asp Gly Ser Gly Gly Xaa Xaa Xaa Xaa Xaa Xaa Xaa Xaa Xaa Xaa
  1               5                  10                  15

Gly Ala Pro Ser Gly Ala Glu Thr Val
            20                  25

(2) INFORMATION FOR SEQ ID NO:7:

(i) SEQUENCE CHARACTERISTICS:
            (A) LENGTH: 10
            (B) TYPE: AMINO ACID
            (D) TOPOLOGY: LINEAR (ii) MOLECULE TYPE:
            (A) DESCRIPTION: PEPTIDE (iii) HYPOTHETICAL: YES
```

(xi) SEQUENCE DESCRIPTION: SEQ ID NO: 7:

Arg His Glu Asp Gly Asp Trp Pro Arg Val
1               5                   10